(12) United States Patent
Bell et al.

(10) Patent No.: US 7,539,584 B2
(45) Date of Patent: May 26, 2009

(54) VOLUME BASED EXTENDED DEFECT SIZING SYSTEM

(75) Inventors: Ernest Bell, Wellesley, MA (US); Neil Judell, Newtonville, MA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

(21) Appl. No.: 11/525,257

(22) Filed: Sep. 21, 2006

(65) Prior Publication Data
US 2007/0179740 A1  Aug. 2, 2007

Related U.S. Application Data

(63) Continuation-in-part of application No. 11/321,689, filed on Dec. 29, 2005, now Pat. No. 7,302,360, which is a continuation-in-part of application No. 10/971,694, filed on Oct. 22, 2004, now Pat. No. 7,184,928.

(60) Provisional application No. 60/514,289, filed on Oct. 24, 2003.

(51) Int. Cl.
*G06F 3/00* (2006.01)

(52) U.S. Cl. .................. 702/81; 702/83; 702/182; 702/183

(58) Field of Classification Search .......... 702/11, 702/159, 166, 179, 193, 196, 81, 83, 182, 702/183; 250/559.46; 356/237.1–237.5; 282/149; 700/279
See application file for complete search history.

(56) References Cited

U.S. PATENT DOCUMENTS

| | | | | |
|---|---|---|---|---|
| 5,712,701 | A | | 1/1998 | Clementi et al. ............. 356/237 |
| 6,118,525 | A | * | 9/2000 | Fossey et al. ............. 356/237.2 |
| 6,529,270 | B1 | * | 3/2003 | Bills ........................ 356/237.2 |
| 6,597,448 | B1 | * | 7/2003 | Nishiyama et al. ........ 356/237.4 |
| 6,888,627 | B2 | * | 5/2005 | Leslie et al. ............. 356/237.2 |
| 6,894,302 | B2 | * | 5/2005 | Ishimaru et al. ......... 250/559.46 |
| 2003/0058455 | A1 | | 3/2003 | Ebihara et al. ............. 356/601 |

* cited by examiner

*Primary Examiner*—Carol S Tsai
*Assistant Examiner*—Felix E Suarez
(74) *Attorney, Agent, or Firm*—Luedeka, Neely & Graham, P.C.

(57) ABSTRACT

A system and method for sizing semiconductor wafer defects combines contiguous light intensity values over a defect area of the wafer to provide a defect sizing metric. The light intensity values resulting from a light source applied to the wafer are summed and the summation is compared to known metric values related to known defect sizes. The result of the comparison provides an estimate for the defect size under consideration. The combination of the light intensity values produces defect sizing estimates in saturated and unsaturated ranges of operation for the wafer inspection equipment. Calculations applied to the combined light intensity values vary depending upon whether the light intensity component is from a saturated or an unsaturated measurement. The defect sizing metric can be applied continuously in saturated and unsaturated ranges of operation to avoid additional processing steps, such as recalibration of the inspection equipment.

12 Claims, 14 Drawing Sheets

US 7,539,584 B2

VOLUME BASED EXTENDED DEFECT SIZING SYSTEM

CROSS REFERENCE TO RELATED APPLICATIONS

This application is a continuation-in-part application of U.S. patent application Ser. No. 11/321,689 filed Dec. 29, 2005 now U.S. Pat. No. 7,302,360 entitled DEFECT SIZE PROJECTION, which is a continuation-in-part application, of U.S. patent application Ser. No. 10/971,694 filed Oct. 22, 2004, now U.S. Pat. No. 7,184,928 entitled EXTENDED DEFECT SIZING, which claims benefit of U.S. Provisional Patent Application No. 60/514,289 filed Oct. 24, 2003 entitled EXTENDED DEFECT SIZING.

STATEMENT REGARDING FEDERALLY SPONSORED RESEARCH OR DEVELOPMENT

Not applicable

BACKGROUND OF THE INVENTION

1. Field of Invention

The present invention relates generally to systems and methods of inspecting semiconductor wafers, and relates more specifically to a semiconductor wafer inspection system, and method capable of detecting and measuring wafer defect's in which the scattering power of the defect exceeds the dynamic range of the system.

2. Description of Related Art

Systems and methods of inspecting workpieces and especially semiconductor wafers are known for detecting and measuring defects occurring on a surface of a semiconductor wafer. For example, a conventional laser-based surface scanning inspection system is typically configured to detect localized light scatters on a semiconductor wafer surface. Such localized light scatters may be indicative of one or more defects on the wafer surface that may render an integrated circuit(s) (IC) fabricated on the wafer to be inoperative. In a typical mode of operation, the conventional surface scanning inspection system sweeps a laser light beam in a predetermined direction, while the wafer being inspected rotates under the swept beam at an angle of about 90° to the predetermined sweep direction. Next, the conventional surface scanning inspection system detects a light beam reflected from the wafer surface, and samples the detected signal in both the predetermined direction of the swept beam and in the direction of rotation to obtain a two-dimensional array of data. When the light beam sweeps over a defect on the wafer surface, the data obtained by the wafer inspection system generally corresponds to the beam shape of the laser spot power at the wafer surface. This is because such wafer surface defects are generally much smaller than the spot size of the laser beam. After the conventional surface scanning inspection system has detected a defect, the system may attempt to measure the size of the defect by determining the value of the maximum scattering power of the defect, and may also determine the location of the defect on the surface of the wafer.

One drawback of the above-described conventional laser-based surface scanning inspection system is that the maximum scattering power of a detected defect may exceed the dynamic range of the system. As a result, the electronics within the wafer inspection system may saturate, thereby causing at least some of the defect size measurements performed by the system to be at a power level at which the measurements become nonlinear due to the saturation effects.

One way of addressing the effects of saturation on defect size measurements made by the conventional laser-based surface scanning inspection system is to employ a data extrapolation technique. However, such data extrapolation techniques are often difficult to perform in conventional wafer inspection systems. Alternatively, the conventional surface scanning inspection system may perform a nonlinear least squares fit of the measurements to a given Gaussian shape, which may be characterized by a number of parameters including an estimated amplitude, an estimated inverse correlation matrix, and an estimated pulse center location. However, conventional algorithms for performing such nonlinear least squares fit techniques often require a significant amount of processing time. Further, relatively small changes in the data resulting from, e.g., noise or a non-ideal signal, may lead to significantly large changes in the estimated parameters.

One methodology that can measure very large defects takes advantage of correlations between a scatter light response for a defect of unknown size, and a scatter light response for a defect of known size. For these large defects, a set-point threshold for scatter light intensity, or the equivalent voltage representation is used to contribute to defining a scatter light response area where the set-point threshold is exceeded. The defined response area is compared to response areas for known defect sizes, determined through calibration processes, and an estimated size of the measured unknown defect can be obtained. The methodology uses an empirical calibration between area and defect or particle size, and has proven to be quite robust. There is a drawback to the methodology in that it adds some difficulty because it uses a completely separate calibration process, which can be time consuming and cumbersome.

Another methodology calculates the area of a cross section of a pulse shape representation of the scatter light response at multiple non-saturated signal levels. The methodology calculates a fit line for area versus logarithm of the signal level. The fit line and non-saturated measurements are used to extrapolate to a pulse cross-section of zero area to estimate peak voltage corresponding to a peak of the pulse shape representation. The methodology also incorporates a verification of the slope of the fit line to match a slope from an expected Gaussian pulse response. This methodology has the drawback of requiring an unclipped or unsaturated signal level. If the signal is clipped, correction of areas for filter effects is imperfect and performance may be degraded. This methodology is also limited in range over which extrapolation is useful, as well as being computationally intensive.

Another technique uses an area of a scatter light response cross section at a single unsaturated signal level and then extrapolates to determine a response peak using a slope expected from a Gaussian pulse response. However, this technique also uses an unclipped signal and can be extremely sensitive to variations from an ideal Gaussian response.

It would therefore be desirable to have an improved system and method of inspecting semiconductor wafers that can measure the size and determine the location of a defect on a surface of a semiconductor wafer while avoiding the drawbacks of conventional wafer inspection systems and methods.

BRIEF SUMMARY OF THE INVENTION

Briefly described, there is provided in accordance with the present disclosure a system and method for sizing semiconductor wafer defects that combines contiguous light intensity values over a defect area of the wafer to provide a defect sizing metric. The light intensity values resulting from a light source applied to the wafer are summed and the summation is compared to known metric values related to known defect sizes. The result of the comparison provides an estimate for the defect size under consideration. The combination of the light intensity values produces defect sizing estimates in saturated and unsaturated ranges of operation for the wafer inspection equipment. Calculations applied to the combined light intensity values vary depending upon whether the light intensity component is from a saturated or an unsaturated measurement. The defect sizing metric can be applied continuously in saturated and unsaturated ranges of operation to avoid additional processing steps, such as recalibration of the inspection equipment.

According to an exemplary embodiment of the present disclosure, a size of a sample defect or particle on a surface of a wafer is estimated by deriving an intensity response shape volume value for the sample particle based on a three-dimensional intensity response shape. The three-dimensional intensity response shape is representative of the intensity of scatter light generated as a laser light traverses the sample particle. The intensity response shape may be defined as a three-dimensional shape comprising the outline and volume of a region of space having as two of its coordinates a two-dimensional location on a wafer at which the scatter light intensity is measured, the third coordinate being the intensity response measured at the location.

A threshold detection intensity may be used to qualify the intensity response shape volume, such as by forming the response volume mapping with scatter light intensity values that are above a given threshold. For example, the threshold may be used to help eliminate low level "haze" or noise that might cause spurious scatter light intensity readings.

The estimated defect or particle size may be obtained according to the following process. The scatter light response is mapped to a three-dimensional representation that tends to be formed as a pulse shape. The sample particle size estimate is based on the intensity response shape volume value derived from the pulse shaped mapping representation for the sample particle. The system and method identifies a relationship between defect or particle size and intensity response shape volume, using particles of known sizes and intensity response shape volume values associated with the known particle sizes. The system and method uses the relationship between the particle size and intensity response shape volume to identify a particle size that can be associated with the intensity response shape volume value obtained for the sample particle.

According to another exemplary embodiment, a method for determining the defect size includes combining a contiguous group of light intensity responses resulting from application of a light source to a surface of the wafer to obtain a representative value. The method compares the representative value to known values related to known defect sizes to obtain a measured defect size. The representative value may be a summation of the light intensity responses for a scanned defect area that results in a volume value. Each light intensity measure is taken in a discrete area that is defined by the in-scan spacing and cross-scan pitch. The light intensity responses may be filtered prior to being combined.

The combined light intensity responses are compensated if there are saturated measurements included in the response. The compensation is based on the recognition that the combination is linear for estimating defect sizes when not saturated, and semi-logarithmic when saturation components are present.

The comparison of the measured combination with known combinations related to known defect sizes may be based on one or more response curves. Alternately, or in addition, the comparison may be based on one or more tables for comparing the representative value to the known values.

According to an aspect of the disclosed system and method, a defect sizing metric contributes to providing a sample particle size estimate. The defect sizing metric is developed based on the volume of the portion of the intensity response shape that is above a threshold detection intensity. The detected light is filtered to produce the volume based sizing metric using an intensity response shape volume value for defect particles. The shape volume values are mapped to a defect size. The mapping may then be used to estimate sample defect sizes.

The intensity response shape volume values are formed by obtaining filtered signals representative of the intensity of light scattered on a surface of the wafer at various surface locations. The intensity response shape volume value is the volume of the portion of the intensity response shape that is above a threshold detection intensity. For example, a set of filtered signals associated with contiguous surface locations with intensity values exceeding a background haze level are identified. Locations of potential defects are determined based on the representations of the filtered signals. Each filtered signal is associated with an area of the surface location, which has a particular light intensity response value. The value is multiplied by an amount associated with a signal intensity level at the surface location to obtain a signal volume value. The volume values from all the contiguous locations in the set of filtered signals are summed to create an intensity response shape volume value. The summed volume values form a map that can be used to estimate sample defect sizes.

Estimation of sample defect sizes is performed by identifying a relationship between defect or particle size and intensity response shape volume. The known intensity response shape volume value for defects or particles of known sizes is used together with a relationship between particle size and intensity response shape volume. The known values and the relationship contribute to identifying a particle size associated with the intensity response shape volume value obtained for the sample particle.

According to one aspect of the present invention, a threshold value may be selected at which intensity responses are subject to being clipped. The relationship between particle size and intensity response shape volume permits estimates to be made for filtered responses above a threshold level. Various constants that are defined by system parameters contribute to identifying a clipping threshold value used in calculating the volume value.

The extended dynamic range obtained through estimates using the relationship between particle size and intensity response shape volume permit the equipment to have an extended factor of operation. The extended factor is a function of the peak of an intensity response to a particle of known size without clipping, and the clipping intensity level. For responses below the clipping threshold, as defined by system characteristics or parameters, a linear relationship exists between the intensity response shape volume values and the extended factor with which they are associated. Above the clipping threshold level, a linear relationship exists between intensity response shape volume values and the logarithm of the extended factor with which the values are associated. Volume values are calculated based on either the linear or semi-logarithm relationship, depending on whether the measured intensity is clipped.

Once the volume sizing metric is calculated, a size of a sample defect can be assigned based on a value of the volume sizing metric. The relationship between particle size and intensity response shape volume can be mapped with a response curve that relates intensity response shape volume values to the extended factor for particle size. The response curve may be represented in linear form or semi-log form to obtain intensity response shape volume values below and above a system clipping threshold, respectively.

Alternately, or in addition, a table having representative intensity response shape volume values and extended factor values for particle sizes may be used to obtain the defect sizing estimate.

BRIEF DESCRIPTION OF THE SEVERAL VIEWS OF THE DRAWINGS

The invention will be more fully understood with reference to the following Detailed Description of the Invention in conjunction with the drawings of which.

DETAILED DESCRIPTION OF THE INVENTION

A system and method of inspecting a semiconductor wafer is disclosed that is capable of measuring the size and determining the location of a defect on a surface of a semiconductor wafer. The presently disclosed wafer inspection system can perform such sizing and locating of wafer surface defects whether or not the scattering power associated with the defect exceeds the dynamic range of the system.

Figure 1:
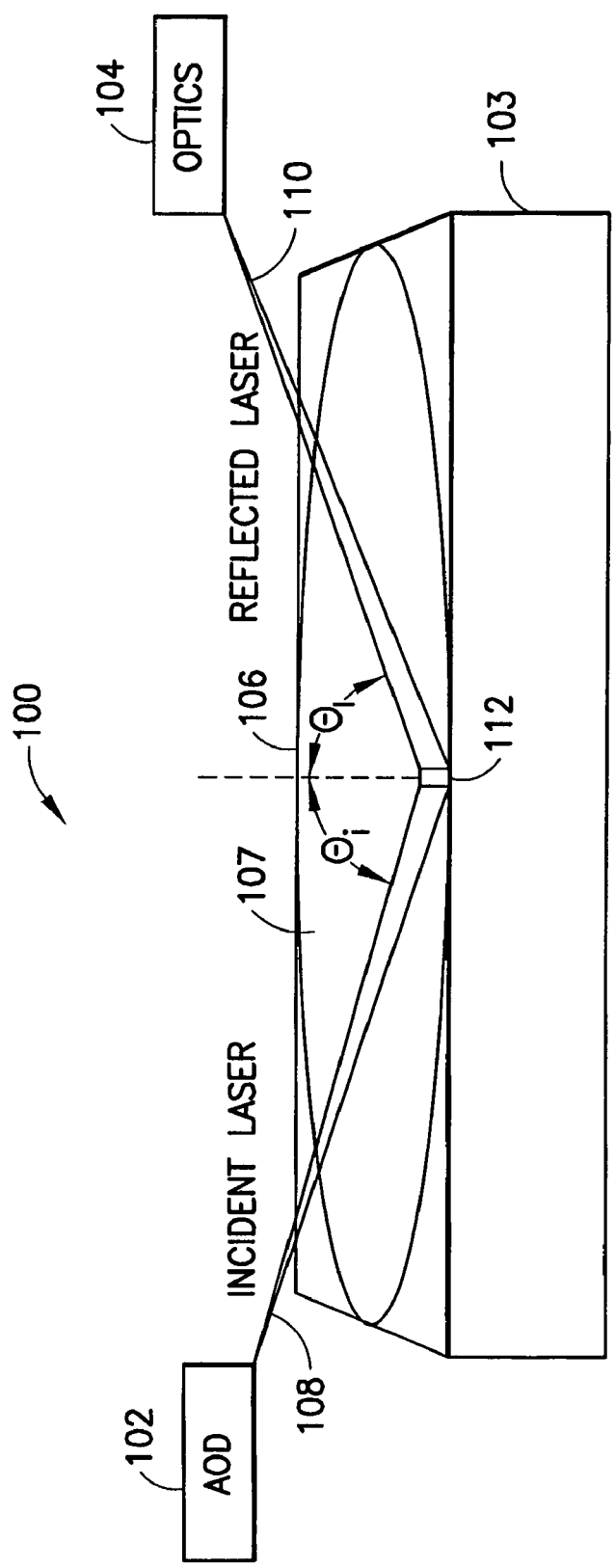
FIG. 1 is a block diagram of a laser-based wafer surface scanning inspection system according to the present invention, in which the system performs a scan of a laser beam on a surface of a semiconductor wafer to detect defects on the wafer surface.

FIG. 1 depicts an illustrative embodiment of a laser-based wafer surface scanning inspection system 100, in accordance with the present invention. In the illustrated embodiment, the surface scanning inspection system 100 comprises an optical module including a surface scanning mechanism 102, and optics 104. Optics 104 include a light detector with a channel for detecting reflected light, often referred to as a "light channel". A light detector with a channel for detecting scattered light, often referred to as a "dark channel" is also included in optics 104. For example, the surface scanning mechanism 102 may be an acousto-optic deflector (AOD) or any other suitable surface scanning mechanism, and the optics 104 may comprise a quadcell photodetector or any other suitable light detector. As shown in FIG. 1, the AOD 102 is configured to emit at least one collimated beam of laser light 108 toward a surface 107 of a semiconductor wafer 106 at an oblique angle of incidence $\theta_i$. Further, the optics 104 are configured to detect a light beam 110 specularly reflected from the wafer surface 107 at an angle of reflection $\theta_r$. Specifically, the optics 104 are configured to detect specular distortions in the reflected light beam 110. It is noted that the wafer 106 may also be inspected from the backside by inverting the wafer in the surface scanning inspection system 100.

For example, the AOD 102 may include a solid state laser such as a 532 nm wavelength diode-pumped solid state laser, or any other suitable type of laser. In the illustrative but not necessarily preferred embodiment, the AOD 102 emits the laser light beam 108 to produce a focused laser spot having a diameter of about 30 microns for scanning the wafer surface 107, in which the incident angle $\theta_i$ of the emitted light beam 108 is about 65 degrees. It should be understood that the laser light beam 108 may alternatively be emitted by the AOD 102 at any suitable angle of incidence to produce any suitable spot size on the wafer surface. The surface scanning inspection system 100 further includes a theta stage 103 upon which the wafer 106 is held during inspection. The theta stage 103 is configured to rotate and to translate the wafer 106 through a scan line 112 produced by the AOD 102, thereby generating a spiral pattern of light used to inspect the wafer surface 107. The theta stage 103 includes an encoder such as an optical encoder that provides counts indicative of the rotational position of the stage 103 relative to a predetermined reference point. It is noted that the structure and operation of the theta stage 103 are known to those skilled in this art and therefore need not be described in detail herein.

Figure 2:
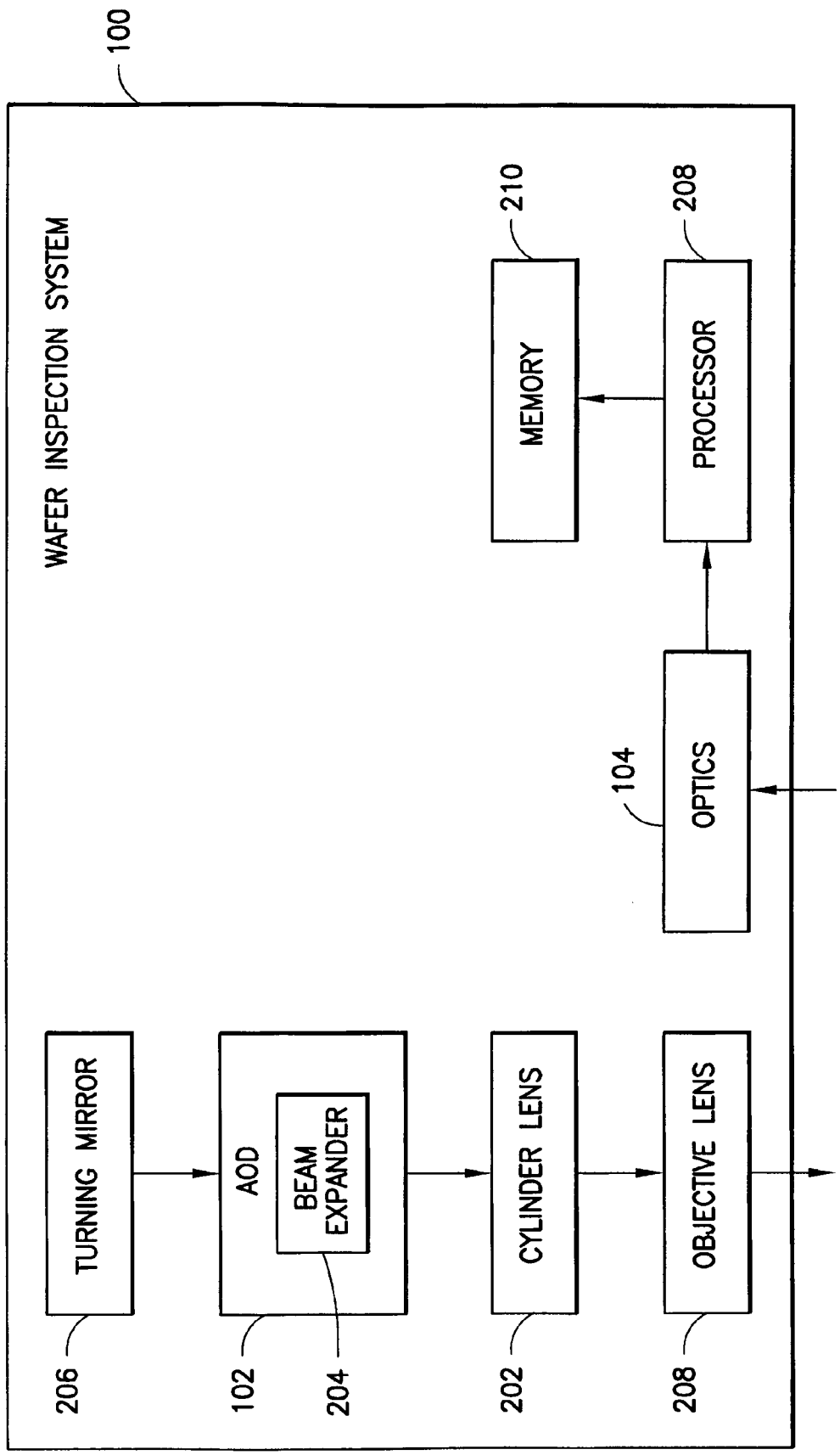
FIG. 2 is a functional illustration of components included in the surface scanning inspection system of FIG. 1.

FIG. 2 depicts a plurality of functional components included in the above-described surface scanning inspection system 100 (see FIG. 1). As shown in FIG. 2, the surface scanning inspection system, shown as Wafer Inspection System 100, comprises a turning mirror 206, the AOD 102 including a beam expander 204, a cylinder lens 202, an objective lens 208, the optics 104, and a processor 208 and associated memory 210. In the illustrated embodiment, the AOD 102 is configured to generate the narrow angle light beam 108 by exciting a crystal with a high frequency sound wave. The beam expander 204 is configured to expand the light beam 108 before the beam enters an aperture of the AOD 102 to obtain a desired angle of deflection. The cylinder lens 202 is disposed at the output of the AOD 102, and is configured to compensate for parasitic cylinder lens loss that may be induced by the deflector. The scan is relayed through the objective lens 208 to the surface 107 of the wafer 106 (see also FIG. 1). The optics 104 are configured to receive the reflected light beam 110, and to detect any losses in light intensity resulting from specular distortion or deflection of the light beam 110.

In the illustrative but not necessarily preferred mode of operation, the optics 104 (see FIG. 1) are also configured to detect localized light scatters from the surface 107 of the wafer 106. For example, such localized light scatters may be indicative of one or more defects on the wafer surface 107 that may render an integrated circuit(s) (IC) fabricated on the wafer 106 to be inoperative. Specifically, the AOD 102 emits the laser light beam 108 toward the wafer surface 107 at the angle of incidence $\theta_i$ and sweeps the light beam 108 in a predetermined radial direction, while the theta stage 103 rotates under the swept beam 108 at an angle of about 90° to the predetermined radial direction. Next, the optics 104 detect the laser light beam 110 reflected from the wafer surface 107 at the angle of reflection $\theta_r$, and detects the light scattered from the wafer surface and samples the detected signal in both the radial and rotational directions to obtain a two-dimensional array of data. The scattered light from the wafer surface is detected in the optics 104 in a dark channel. It is noted that the sampling of the data is generally non-orthogonal. The processor 208 included in the surface scanning inspection system 100 is operative to process the sampled data by executing one or more programs out of its associated memory 210 (see FIG. 2).

In the presently disclosed embodiment, the corresponding location of each data sample on the wafer surface 107 is expressed as $$x_{in,xs}, y_{in,xs}, \quad (1)$$

in which the index "in" designates samples in the radial or "in scan" direction, and the index "xs" designates samples in the tangential or "cross scan" direction.

When the light beam 108 sweeps over a defect on the wafer surface 107, the data samples obtained by the surface scanning inspection system 100 generally correspond to the beam shape of the laser spot on the surface 107. This is because wafer surface defects are normally much smaller than the spot size of the laser beam 108. For example, the data samples may be represented by a geometric Gaussian shape that is non-isotropic due to the angle of incidence $\theta_i$ and the non-orthogonal sampling of the data.

The locations $(x_{in,xs}, y_{in,xs})$ of the data samples on the wafer surface 107 may be expressed as a column vector, i.e., $$\vec{z} = \begin{bmatrix} x_{in,xs} \\ y_{in,xs} \end{bmatrix}. \quad (2)$$

Accordingly, the optical laser spot power at the wafer surface 107 may be expressed as $$\text{power}(\vec{z}) = P_0 \exp(-(\vec{z} - \vec{z}_0)' R^{-1} (\vec{z} - \vec{z}_0)), \quad (3)$$

in which "$P_0$" is the maximum scattering power of the defect, "$\vec{z}_0$" denotes the location of the defect, and "R" is a positive definite symmetric matrix describing the beam shape.

For example, if a laser spot is Gaussian, meaning that the intensity profile of the laser spot is a two-dimensional Gaussian function, and has a density of density(x)=$e^{-x^2/2\sigma^2}$, then the 1/$e^2$ full-width may be expressed as 4$\sigma$. For an illustrative 50 micron 1/$e^2$ full-width beam, which strikes a wafer at a 65-degree incident angle, then the density at the wafer surface may be expressed as $$\text{density}(x,y) = e^{-x^2/2(12.5\mu)^2} e^{-y^2/2(12.5\mu/\cos(65°))^2}. \quad (4)$$

Equation (4) above may be rewritten as $$\text{density}(x, y) = \exp\left(\begin{bmatrix} x \\ y \end{bmatrix}' \begin{bmatrix} (12.5\mu)^2 & 0 \\ 0 & (12.5\mu/\cos(65°))^2 \end{bmatrix}^{-1} \begin{bmatrix} x \\ y \end{bmatrix}\right). \quad (5)$$

Accordingly, for this illustrative example, $$R = \begin{bmatrix} (12.5\mu)^2 & 0 \\ 0 & (12.5\mu/\cos(65°))^2 \end{bmatrix}. \quad (6)$$

In the event the sampled data comprises non-saturated data (i.e., the data sampling is linear), the surface scanning inspection system 100 may determine the value of $P_0$ in equation (3) above by identifying the largest value in the collection of measured data points, which may be expressed as $$\text{power}(x_{in,xs}, y_{in,xs}). \quad (7)$$

This technique for determining the value of $P_0$ generally does not yield useful results when the maximum scattering power of a detected defect exceeds the dynamic range of the surface scanning inspection system 100, i.e., when the sampled data comprises saturated data. In practice, the gain of the surface scanning inspection system 100 is set high to permit detection of small defects. Thus, the power level of surface scanning inspection system 100 may be relatively high to detect and measure small defects. As a result, at least some of the defect size measurements performed by the wafer inspection system may be at a power level at which the measurements become nonlinear due to the saturation effects.

Figure 3:
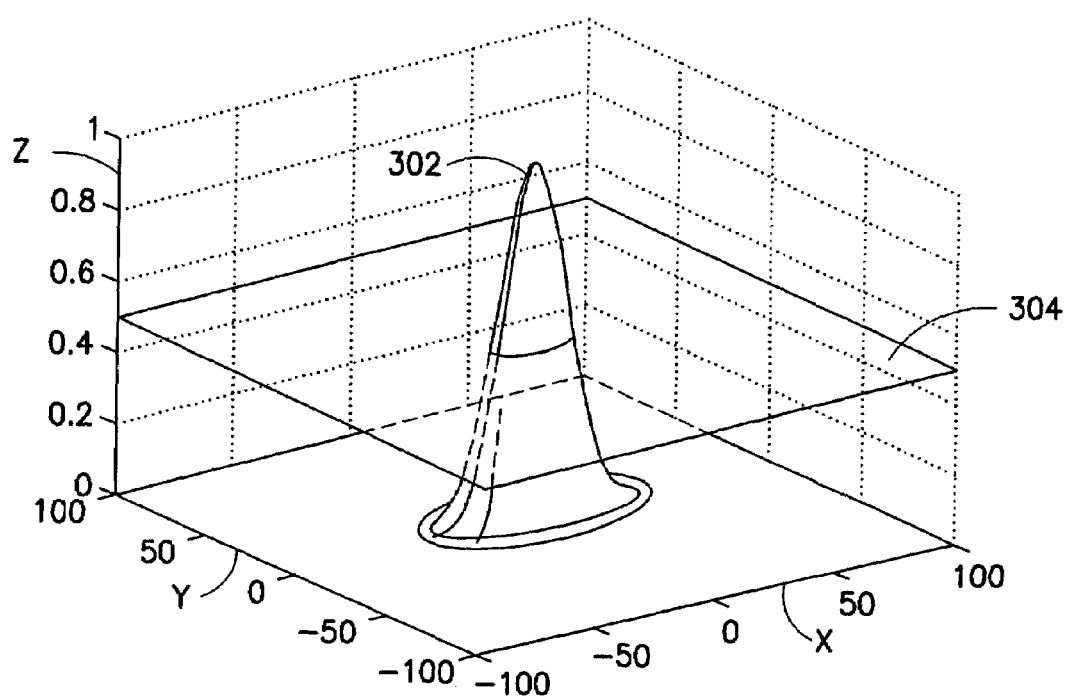
FIG. 3 is a diagram of a first geometric Gaussian shape in three-dimensional space, the first Gaussian shape representing non-saturated data collected by the surface scanning inspection system of FIG. 1.
Figure 4:
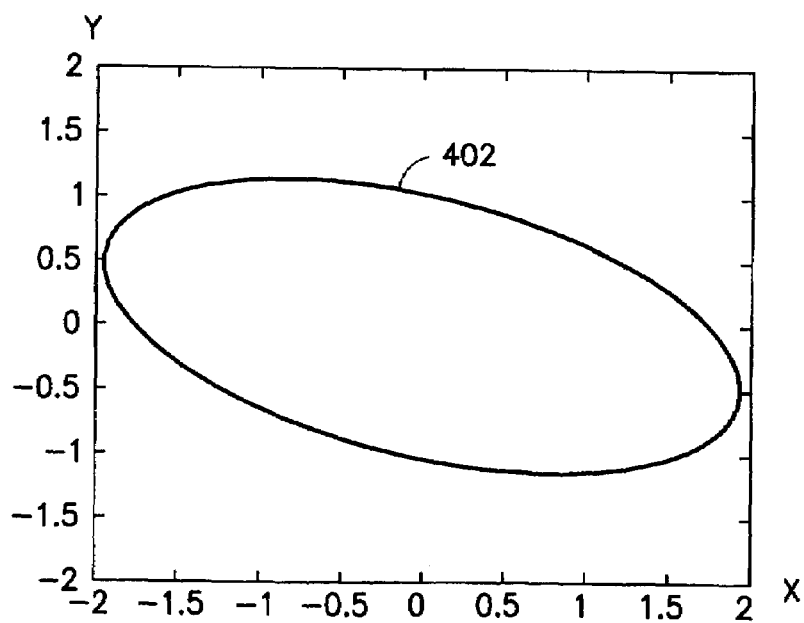
FIG. 4 is a diagram of an elliptical cross-sectional area of the first Gaussian shape of FIG. 3, the cross-sectional area being obtained by conceptually cutting the first Gaussian shape in an x-y plane corresponding to a predetermined height of the Gaussian shape.

One prior technique measures the size and determining the location of a defect on a surface of a semiconductor wafer when the maximum scattering power of a detected defect exceeds the dynamic range of the surface scanning inspection system 100, i.e., the sampled data collected by the wafer inspection system comprises saturated data. FIG. 3 depicts a geometric Gaussian shape 302 in a space defined by x, y, and z axes, in which the Gaussian shape 302 represents non-saturated data collected by the surface scanning inspection system 100 (see FIG. 1). If the Gaussian shape 302 is conceptually cut by an x-y plane 304 at a predetermined amplitude ("cut height") along the z-axis, then the resulting cross-sectional area of the Gaussian shape 302 in the x-y plane 304 has the shape of an ellipse 402 (see FIG. 4). The area of the ellipse 402 may be determined by solving for the area of a region defined by $$\text{power}(\vec{z}) > \text{height}, \quad (8)$$

in which "power($\vec{z}$)" is expressed as indicated in equation (3) above. Substituting this expression for power($\vec{z}$) in equation (8) yields $$(\vec{z} - \vec{z}_0)' R^{-1} (\vec{z} - \vec{z}_0) < \ln(P_0) - \ln(\text{height}). \quad (9)$$

Let $$\text{Area} = \iint_{(\vec{z}-\vec{z}_0)' R^{-1}(\vec{z}-\vec{z}_0) < \ln(P_0)-\ln(height)} d\vec{z}, \quad (10)$$

and $$y = R^{-\frac{1}{2}}(\vec{z} - \vec{z}_0), \quad (11)$$

$$dy = |R|^{-\frac{1}{2}} d\vec{z},$$

$$d\vec{z} = |R|^{\frac{1}{2}} dy.$$

Accordingly, $$\text{Area} = \iint_{|y| < \sqrt{\ln(P_0)-\ln(height)}} |R|^{\frac{1}{2}} dy, \quad (12)$$

$$\text{Area} = \int_0^{2\pi} \int^{\sqrt{\ln(P_0)-\ln(height)}} |R|^{\frac{1}{2}} r \, dr \, d\theta, \text{ and} \quad (13)$$

$$\text{Area} = \pi |R|^{\frac{1}{2}} (\ln(P_0) - \ln(\text{height})). \quad (14)$$

Equation (14) above shows that the area of a geometric Gaussian shape conceptually cut at a predetermined height (e.g., the area of the ellipse 402; see FIG. 4) is a linear function of the natural logarithm (ln) of the predetermined cut height. As indicated by equation (14), the cross-sectional area is equal to zero when the cut height equals the scattering power $P_0$ of the defect. Further, the slope of the line defined by equation (14) is equal to $$\pi |R|^{1/2}, \quad (15)$$

in which "$|R|^{1/2}$" is the square root of the determinant of the positive definite symmetric matrix describing the beam shape. It is noted that "$\pi |R|^{1/2}$" is equal to the "1/e" area of the Gaussian shape. Accordingly, after plotting the area values as a function of the natural logarithm (ln) of the predetermined cut heights, and applying a least squares fit to the plot to form a linear plot, the intercept at which the area is zero is equal to the natural logarithm of the scattering power $P_0$, and the slope of the linear plot is equal to the 1/e area of the Gaussian shape.

Figure 5:
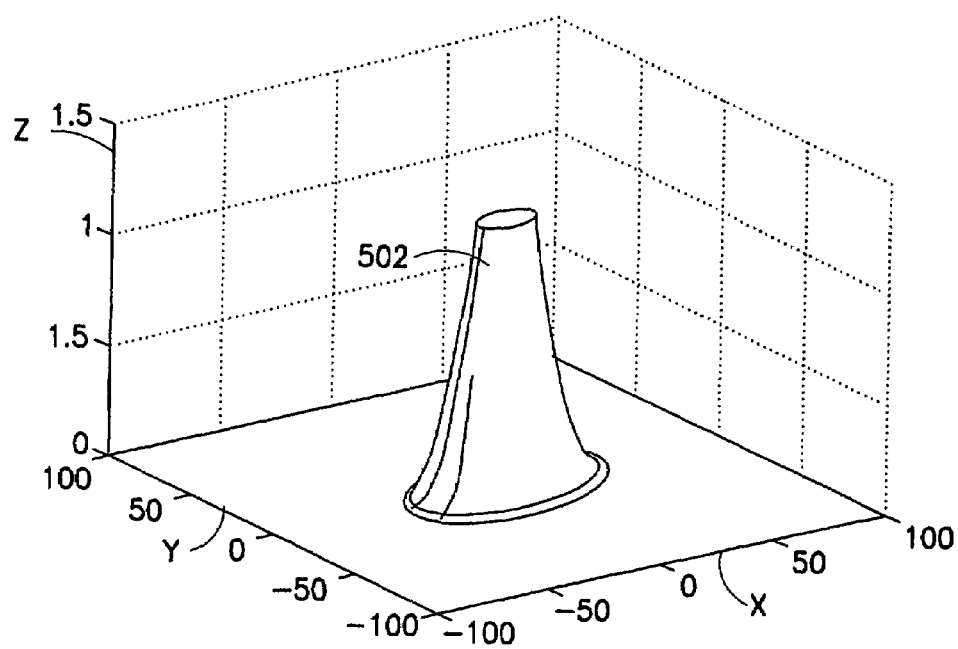
FIG. 5 is a diagram of a second geometric Gaussian shape in three-dimensional space, the second Gaussian shape representing saturated data collected by the surface scanning inspection system of FIG. 1.
Figure 6:
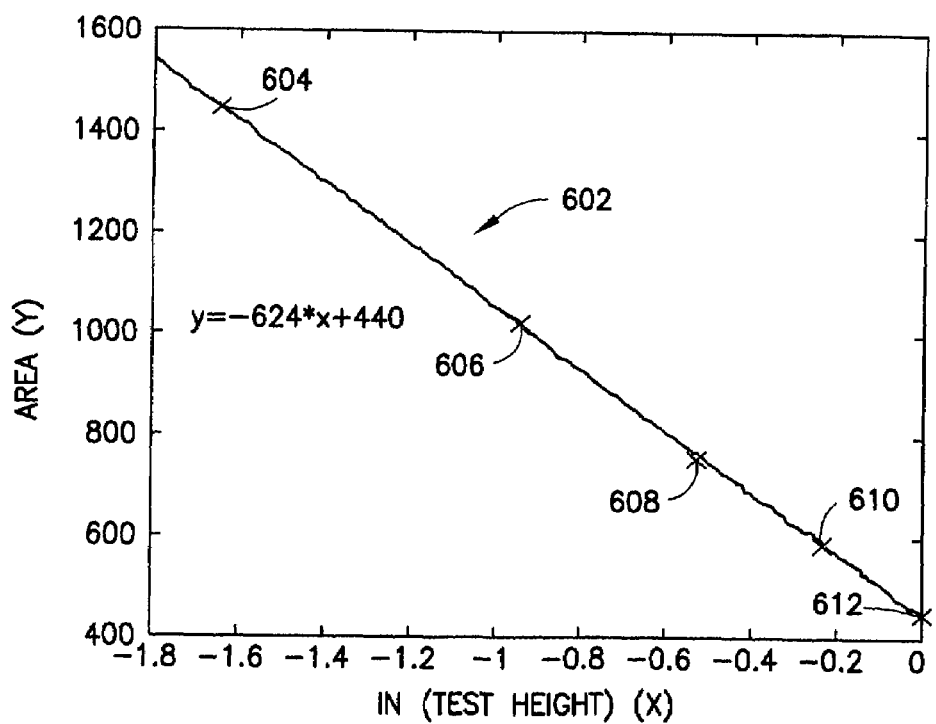
FIG. 6 is a diagram illustrating a linear least squares fit of the data represented by the second Gaussian shape of FIG. 5.

One technique for measuring the size and determining the location of a defect on a semiconductor wafer surface is illustrated by the following example. FIG. 5 depicts a geometric Gaussian shape 502 in x, y, z coordinate space, in which the Gaussian shape 502 comprises saturated data collected by the surface scanning inspection system 100 (see FIG. 1). In this example, the Gaussian shape 502 is conceptually cut in the x-y plane at a plurality of predetermined cut heights along the z-axis, namely, at cut heights of 0.2, 0.4, 0.6, 0.8, and 1.0 units. Next, the respective cross-sectional areas of the Gaussian shape 502 conceptually cut at these predetermined heights are determined. The values of the cross-sectional areas are then plotted versus the natural logarithm (ln) of the respective cut heights, and a least squares fit is applied to the plot to produce a linear plot 602 of the collected data, as depicted in FIG. 6. As shown in FIG. 6, the linear plot 602 includes the data points 604, 606, 608, 610, and 612 corresponding to the predetermined cut heights 0.2, 0.4, 0.6, 0.8, and 1.0, respectively. In this illustrative example, the linear plot 602 may be expressed as $$y = -624x + 440, \quad (16)$$

in which the variable "y" represents the cross-sectional area of the Gaussian shape 502 and the variable "x" represents the natural logarithm of the predetermined cut height.

Accordingly, equation (16) above indicates that the cross-sectional area (y) is equal to zero when the natural logarithm of the cut height (x) equals about 0.705. The cut height at which the cross-sectional area equals zero may therefore be obtained by taking the inverse natural logarithm of 0.705, which is about 2.02. Because the cross-sectional area is equal to zero when the cut height equals the scattering power $P_0$ of a wafer surface defect, as indicated in equation (14) above, $P_0$ is equal to about 2.02. In this example, the actual height of the illustrative Gaussian shape 502 (i.e., the height that would be observed in the absence of saturation effects) is 2.0. Further, the slope of the linear plot 602, as expressed by equation (16) above, is equal to −624, which is the 1/e area of the Gaussian shape. In this example, the actual 1/e area of the Gaussian shape 502 (i.e., the 1/e area that would be observed in the absence of saturation effects) is $200\pi$, or about 628. Based on these results, a correlation coefficient may be calculated as 0.9999. In general, if the correlation coefficient is much less than unity, then the linear least squares fit is considered to be poor. Because the correlation coefficient is equal to 0.9999 in this illustrative example, the linear least square fit is considered to provide an accurate measure of the actual height of the Gaussian shape 502.

The above-discussed methodology extends the linear dynamic range of the wafer scanning system by factor of approximately ten in the optical power domain. By using techniques that involve curve fitting and knowledge of the beam shape, the methodology permits determination of a voltage equivalent magnitude of a defect. With the calculated voltage magnitude, optical models may be used to convert the voltage equivalent magnitude to a scattered power, and then to defect size.

However, the above-described methodology begins to degrade in performance when applied to extend the linear dynamic range of the system beyond the factor of ten. For example, FIGS. 7a-7h illustrate Gaussian pulse responses determined from a light detector where the responses extend beyond a system threshold when measuring larger defects. As can be seen, the larger defects prevent the beam from accurately retaining a Gaussian shape. That is, as the observed defect becomes larger in size, the outlying lower-power sections of the beam influence the curve fit estimations and averages. Because the optics are not perfect, the beam is not perfectly Gaussian, and the imperfections can degrade the accuracy of the above methodology in the case of very large defects.

Other techniques have been used to detect and measure very large defects that produce pulses outside the dynamic range of the equipment. To measure the very large defects, a cross-sectional area of a Gaussian pulse generated by the defect is determined, based on a given set point threshold, or height at which the cross-sectional area is taken. The thus determined cross-sectional area is compared to areas generated under similar conditions for known defects or particle sizes. An estimate for the defect or particle size can be made based on the comparison and interpolation techniques.

While the results of the above-described technique are fairly robust, an empirical calibration is made between the area of the cross-section and the particle size. That is, a completely separate calibration process is used to set up the measurement, since the nature of the very large defect dramatically increases the range of extrapolation for determining pulse height and thus defect sizing. When the correlation coefficient of the previously described methodology is much less than unity, meaning that a very large defect is detected that introduces some nonlinearity into the methodology, the linear least squares fit is considered to be poor. The impact on the methodology can be observed by visualizing the truncated pulse of FIG. 5 as approaching the shape of a column, as seen in FIGS. 7b-7h, for example, indicating a very high pulse, as well as an ill-conditioned fit for the linear relationship used to determine pulse height.

To improve detection of small defects when the gain of surface scanning inspection system 100 is set high, filtering is typically used to reduce shot noise caused by the arrival of discrete photons at the detector. Reliable detection of small defects results from the application of two-dimensional matched filtering to enhance the signal-to-noise ratio. Matched filtering is commonly used for obtaining measurements from systems having additive Gaussian noise. Matched filtering is described in detail in the U.S. Pat. No. 6,529,270, which is entitled APPARATUS AND METHOD FOR DETECTING DEFECTS IN THE SURFACE OF A WORKPIECE and which is hereby incorporated by reference, for background.

The matched filtering is typically performed in two steps related to operation of the surface scanning inspection system 100. First, in-scan matched filtering is applied to the outputs of the optical detectors, followed by cross-scan matched filtering. The output of the optical detectors is a voltage that represents the instantaneous optical power of the received light. The application of the two-dimensional matched filtering tends to decrease the peak values of the input voltage signals representing the instantaneous optical power. Accordingly, even when a saturated response is observed, the two-dimensional matched filtering tends to smooth the aggregate defect light intensity response. A representation of such a smoothed response is illustrated in FIGS. 8a-8h.

The present invention provides a system and method for determining defect size when system measurements exceed the dynamic range of the equipment. The system and method derive an intensity response shape volume value based on a three-dimensional intensity response shape that is representative of the intensity of scatter light generated as a laser light traverses the sample defect. The intensity response shape volume value is used to estimate the defect size based on a relationship of a known intensity response shape volume value related to a known sample particle. The relationship may be used to extend the range of the measuring equipment without extraordinary calibration of the equipment, and is more robust than the previously used estimation techniques.

The intensity response shape volume value may be calculated as the volume of the portion of the intensity response shape that is above a given threshold detection intensity. The disclosed system and method estimates the defect or particle size based on the measured response shape volume value in comparison with a known intensity response shape volume value that corresponds to a known particle size. A set of known intensity response shape volume values and associated known particle sizes develop the relationship that may be used to extend the system measurement capability. By using the measured intensity response shape volume value and the known relationship, large defect sizes can be accurately estimated over a wide range of sizes.

Figure 7B:
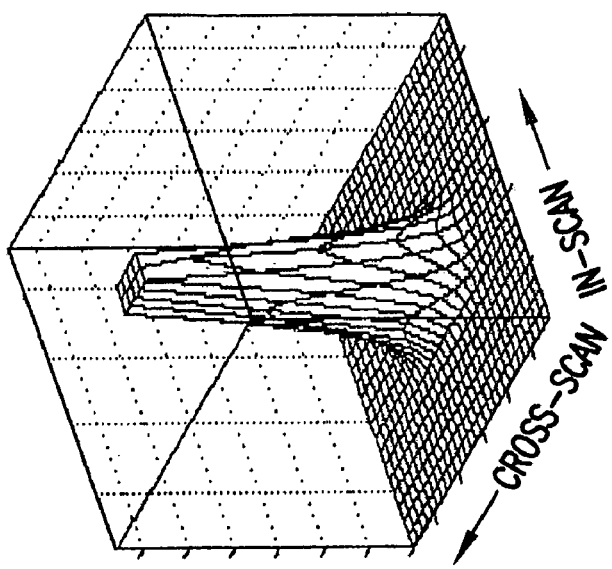
FIGS. 7a-7h are three-dimensional graphs showing various Gaussian response pulses with a clipping threshold height.
Figure 7A:
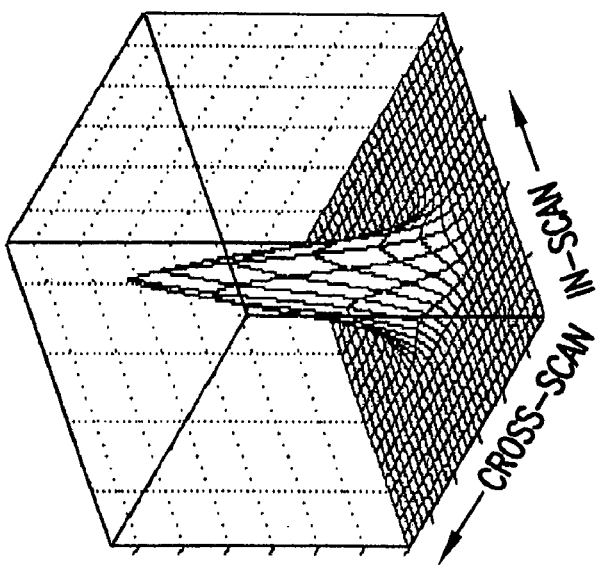
Figure 7D:
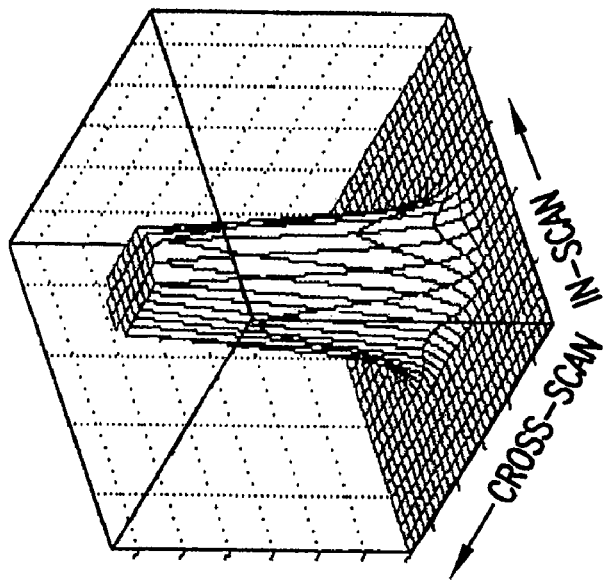
Figure 7C:
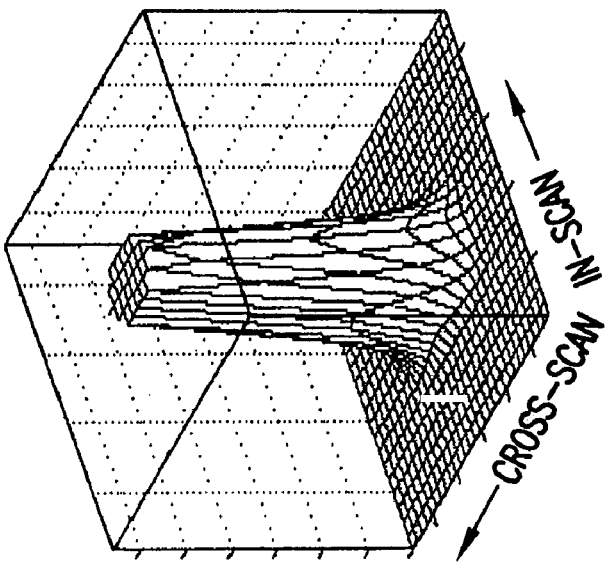
Figure 7F:
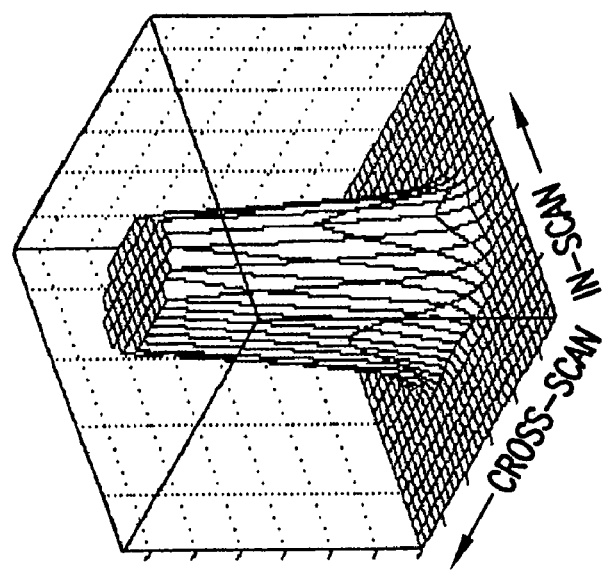
Figure 7E:
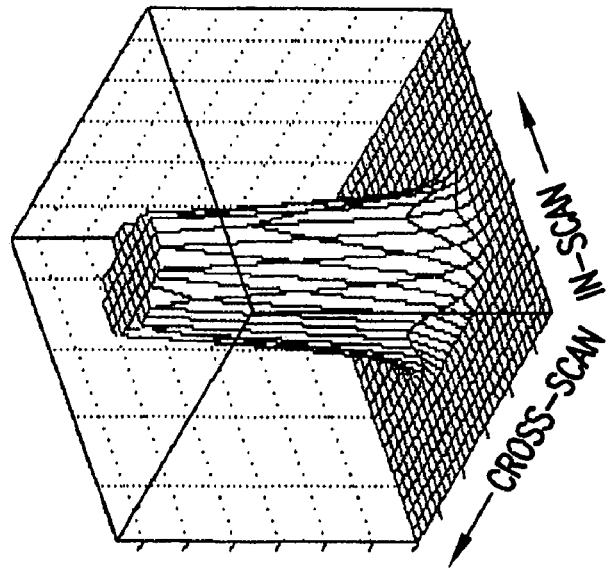
Figure 7H:
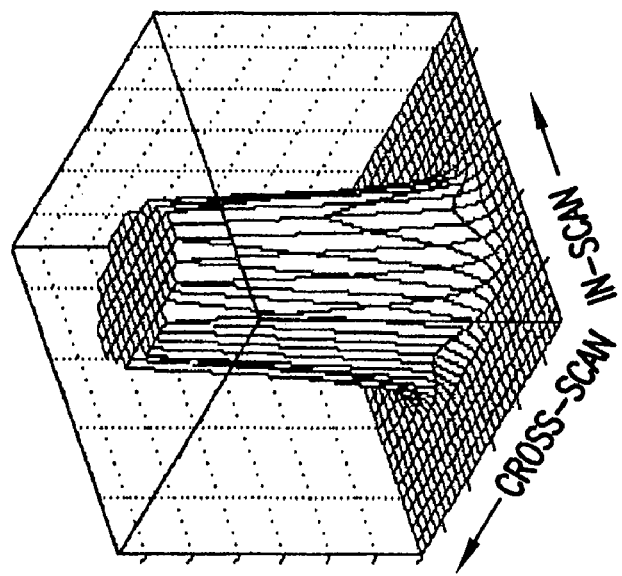
Figure 7G:
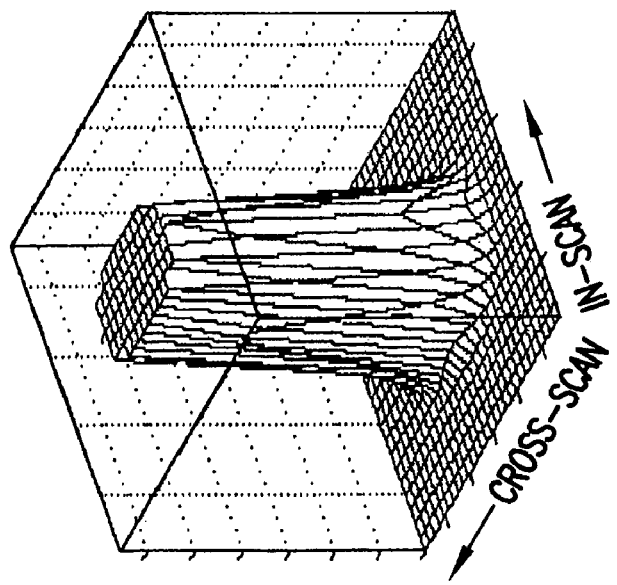
Figure 8B:
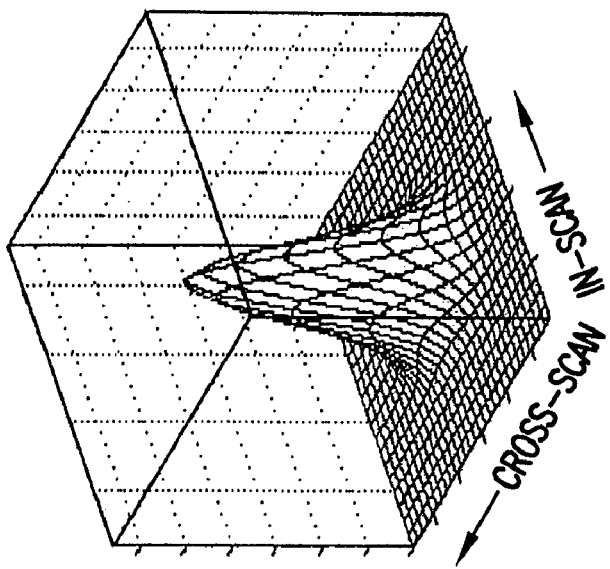
FIGS. 8a-8h are three-dimensional graphs illustrating filtered Gaussian response shape volumes for various clipping thresholds.
Figure 8A:
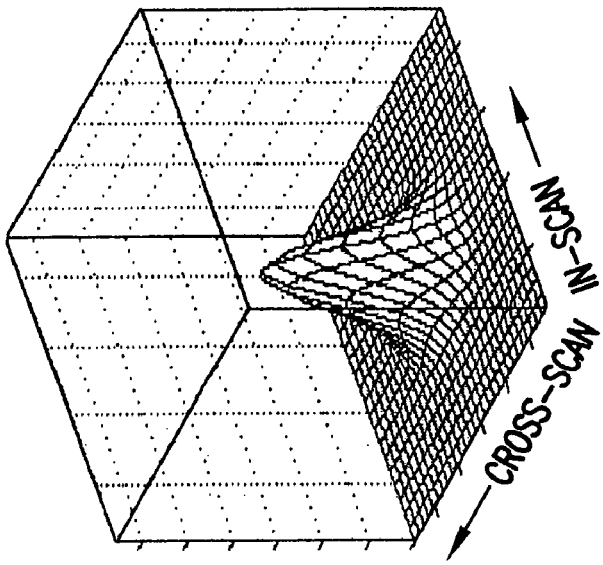
Figure 8D:
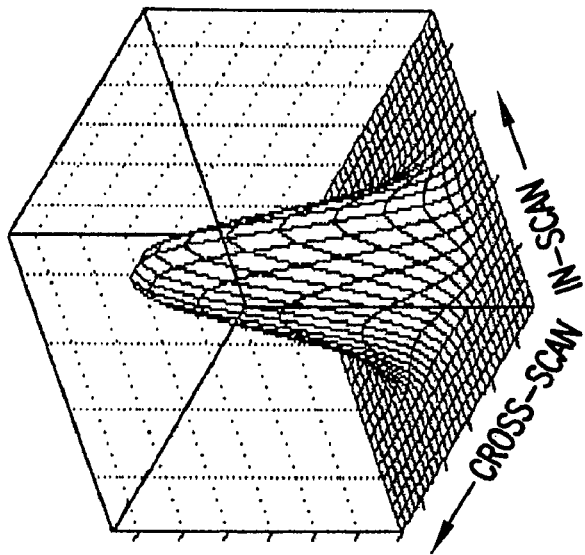
Figure 8C:
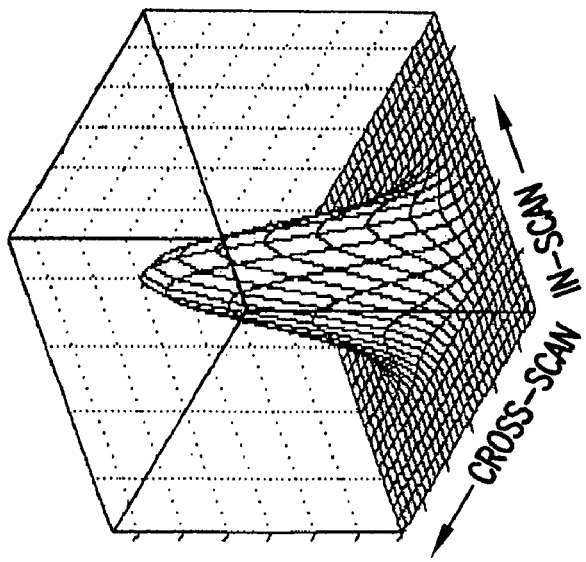
Figure 8F:
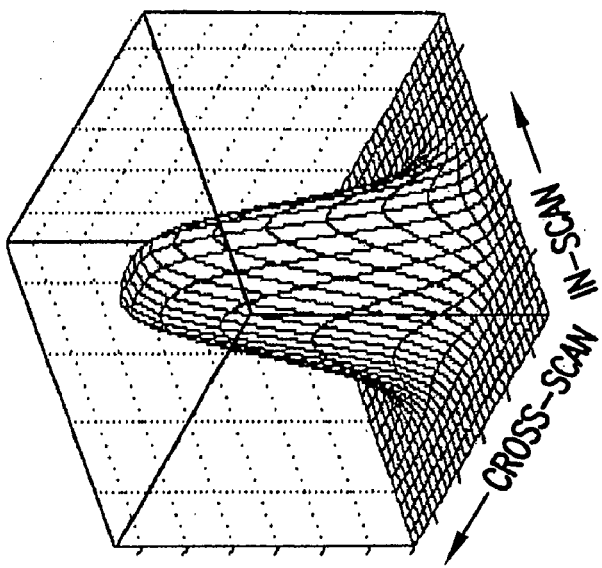
Figure 8E:
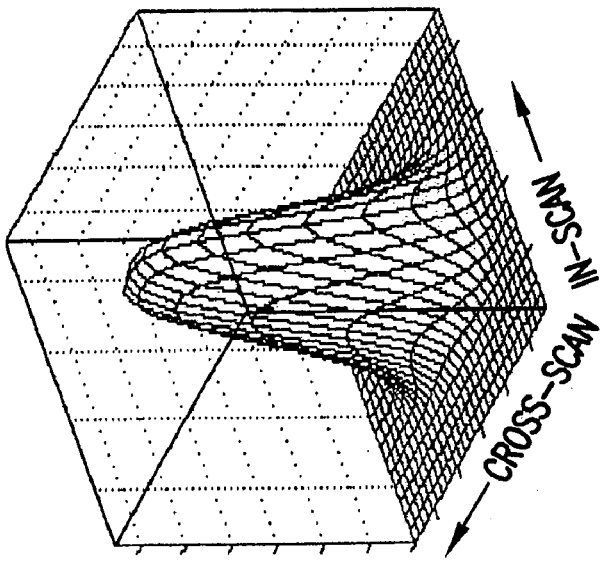
Figure 8H:
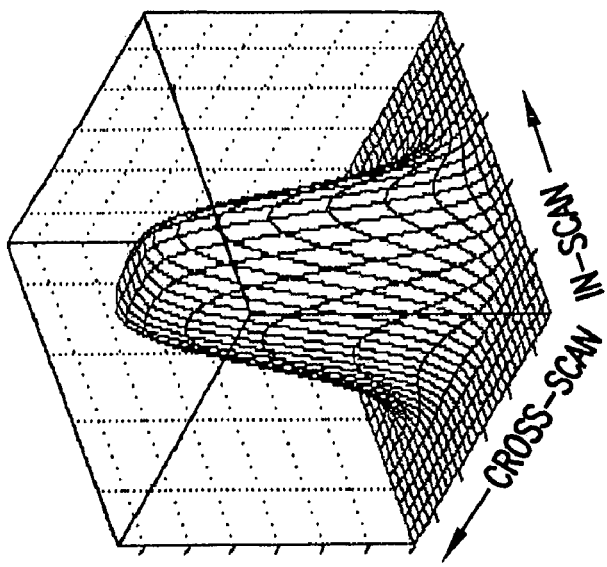
Figure 8G:
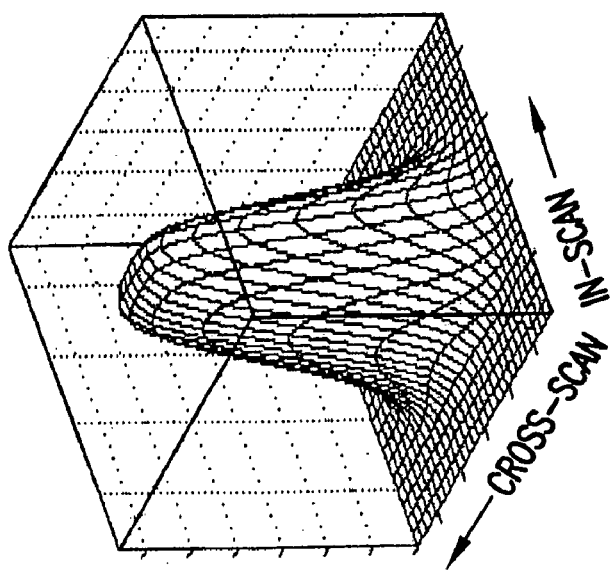

FIGS. 8a-8h illustrate three-dimensional intensity response shapes representative of the intensity of scatter light generated with respect to a defect or particle under examination. FIG. 8a similarly shows the filtered three-dimensional intensity response shape related to an unclipped signal shown in FIG. 7a. FIGS. 8b-8h relate to three-dimensional filtered intensity response shapes corresponding to FIGS. 7b-7h for clipped signals that would have been 2, 5, 10, 20, 50, 100 and 200 times the maximum unclipped signal, respectively.

A volume based sizing metric is formed by creating intensity response shape volume values for known defect particles and mapping the values to a defect size. The mapping is then used to estimate measured defect sizes. The intensity response shape volume values are formed by filtering signals that represent the intensity of light scattered on the surface of the wafer at specific locations. FIGS. 8a-8h are filtered representations of the light intensity response shapes shown in FIGS. 7a-7h, respectively. FIG. 7a shows an unclipped light intensity response, at a maximum unclipped height for the unfiltered intensity response. The filtered signals are grouped together as a set to represent contiguous surface locations where intensity response values exceed a background haze level. The set of signals represent a potential defect location. With a set of filtered signals representing light intensity responses at discrete wafer locations, the disclosed system and method obtains a volume value by combining the set of filtered signals. The volume value is related to the defect or particle size at the surface location from which the set of filtered signals is obtained.

According to one exemplary embodiment, the set of volume values are summed from all the contiguous locations in the set that relate to a given defect. An intensity response shape volume value results. The volume value represents a mapping from light intensity response to defect or particle size to assist with estimating the defect or particle size.

Once the intensity response shape volume value is known, the value is compared to known values associated with defects or particles of known size. The result of the comparison provides an estimate for the size of the defect or particle under examination. A form of interpolation may be used to determine the estimated defect or particle size based on known defect or particle sizes.

According to one exemplary embodiment, the intensity response shape volume value is derived from the portion of the light intensity response that is above a threshold detection intensity. The threshold detection intensity is set to avoid spurious inputs or noise in the light detection optics or devices. Measurements taken above the threshold detection intensity represent defects or particles to be analyzed.

The disclosed system and method works well for both clipped and unclipped signals. When light intensity response signals are unclipped, there is a linear relationship between the calculated volume value and the estimated size of the defect or particle under examination. When light intensity response signals are clipped, there is a semi-log relationship between the calculated volume value on the estimated size of the defect or particle. By knowing a priori the point at which the light detection device or detection system saturates, the appropriate linear or semi-log calculations can be applied to determine the appropriate relationship to use the estimate defect or particle size. In this way, the same metric may be used to estimate defect or particle size in a continuous range that encompasses a saturation point. The continuity of the metric permits defect detection over a wide range of saturated and unsaturated response without having to change detection methods. One advantage of this continuity is the avoidance of time consuming and costly recalibration.

In the range of clipped response, the disclosed system and method extends the range of the detection equipment by an extension factor. When the intensity responses are subject to being clipped at a selected intensity level, the relationship maps intensity response shape volume values to values identified with an extension factor. The extension factor is a function of the peak of an intensity response to a particle x of known size that would have been reached if the response had not been clipped. The extension factor is also a function of the clipping intensity level, which is the intensity level at which the response is clipped. The relationship of the extension factor is $$EF(x) = \frac{p(x)}{C} \quad (17)$$

In equation (17), p(x) equals the intensity response to a particle x of known size that would have been reached if it had not been clipped. C is a constant equal to or related to the clipping intensity level for the surface inspection system. In practice, a continuous relationship for inspection of defects with a pulse response below the threshold and with a pulse response above the threshold may be defined. The intensity response shape volume for particle x is thus equal to $$V(x) = B * EF(x) \quad \text{for } EF(x) < 1 \quad (18a)$$
$$= A * \log_{10}[EF(x)] + B \quad \text{for } EF(x) \geq 1 \quad (18b)$$

In equations (18a) and (18b), A and B are constants defined by characteristics of the surface inspection system. For EF(x)<1, there is linear relationship between intensity response shape volume values and the extension factor with which the volume values are associated. When EF(x) is greater than or equal to 1, there is a linear relationship between intensity response shape volume values and the log of the extension factor with which they are associated.

As an example, if a light intensity response is just clipped, so that p(x)=C, then V(x)=B. Accordingly, the constant B provides a system dependent value that represents the point at which unfiltered light intensity responses begin to saturate. Using the known value for B, the point at which linear or semi-log calculations are applied can be determined.

Figure 9:
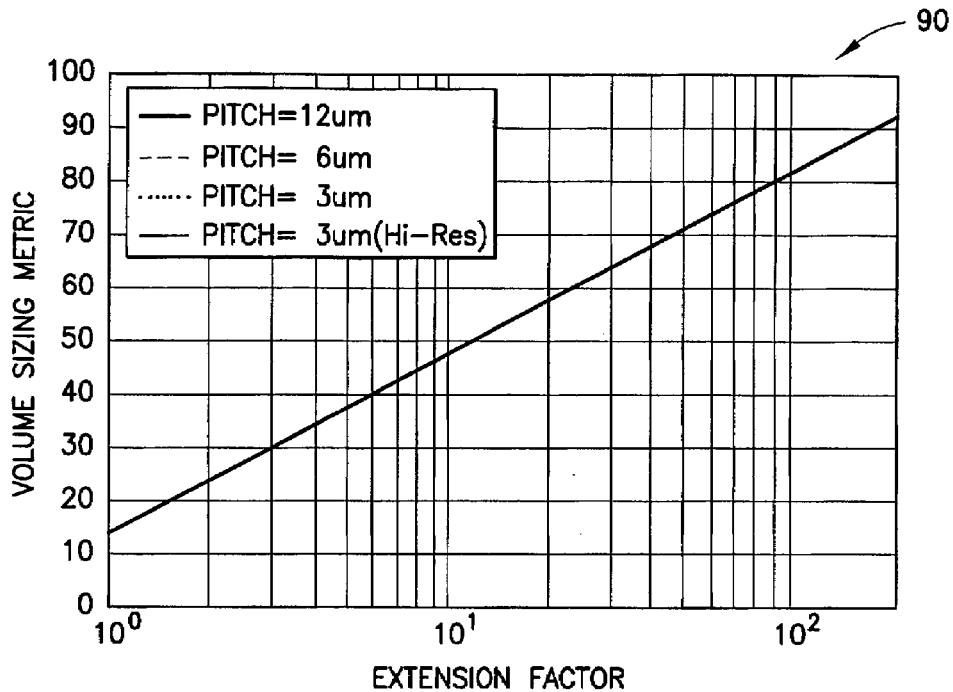
FIG. 9 is a semi-logarithmic graph illustrating volume sizing metric versus extension factor.

Referring now to FIG. 9, graph 90 illustrates the behavior of the volume sizing metric for multiple scanning configurations over a wide range of clipped inputs. As can be seen in graph 90, the relationship between the volume sizing metric and the extension factor is linear with respect to the log of the extension factor. The extension factor is a multiple of the clipping level that the peak of an unclipped response would have reached if it had not been clipped due to system limitations. The extension factor ranges from 1, which indicates that the response is near the edge of being clipped, to a value of 200, indicating severe clipping. The scanning configurations represent cross-scan pitches of 12 μm, 6 μm, and 3 μm, all of them normal in-scan pitch. There is also the representation of a high-resolution configuration with a cross-scan pitch of 3 μm and an in-scan pitch that is ⅓ the normal in-scan pitch. The resulting plot, exemplified in graph 90 approximates a straight line in the semi-log graph, indicating very small variance for the volume sizing metric with respect to a specific scanning configuration. Indeed, the plots for the different scanning configurations fall nearly on top of each other. Accordingly, calibration of the equipment is simplified due to the fact that calibration need not be changed to obtain an accurate result over a wide range of measurements using the disclosed system and method.

Figure 10:
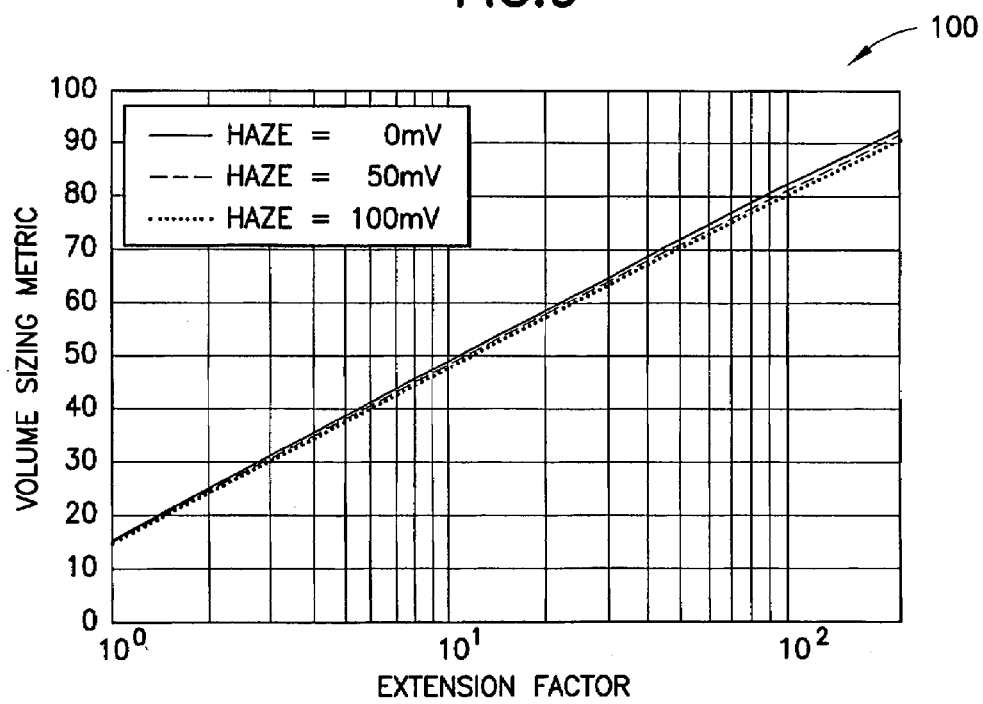
FIG. 10 is a semi-logarithmic graph illustrating volume sizing metric versus extension factor for various haze values.

Referring to FIG. 10, an illustration of background haze on the volume sizing metric is illustrated in a graph 100. The background haze has an impact that reduces the difference between the haze level and the saturation level. The semi-log graph 100 shows plots for haze levels of 0 mV, 50 mV, and 100 mV. The relationship between the volume sizing metric remains linear in semi-logarithmic plot 100 for each haze level, with the slope and offset varying slightly with the haze. For intermediate haze values, interpolation may be used to establish the relationship between volume sizing metric and extension factor.

In addition to haze, spot size of the laser used in the measurement system can have a strong impact on the volume sizing metric. Table 1 below illustrates coefficients that may be used for a linear semi-log relationship between the extension factor and the volume sizing metric for spot sizes that vary from 40 μm to 55 μm, and haze levels that vary from 0 mV to 100 mV.

TABLE 1

Volume = A * log10 (Extension Factor) + B

| | A | B |
|---|---|---|
| spotSize = 40 um | | |
| 0 mv haze: | 24.3247 | 10.5638 |
| 25 mv haze: | 24.2082 | 10.4830 |
| 50 mv haze: | 24.0921 | 10.3995 |
| 75 mv haze: | 23.9737 | 10.3158 |
| 100 mv haze: | 23.8583 | 10.2254 |
| spotSize = 41 um | | |
| 0 mv haze: | 25.5562 | 11.0983 |
| 25 mv haze: | 25.4335 | 11.0144 |
| 50 mv haze: | 25.3123 | 10.9271 |
| 75 mv haze: | 25.1891 | 10.8399 |
| 100 mv haze: | 25.0644 | 10.7513 |
| spotSize = 42 um | | |
| 0 mv haze: | 26.8177 | 11.6473 |
| 25 mv haze: | 26.6894 | 11.5599 |
| 50 mv haze: | 26.5606 | 11.4713 |
| 75 mv haze: | 26.4339 | 11.3782 |
| 100 mv haze: | 26.3010 | 11.2882 |
| spotSize = 43 um | | |
| 0 mv haze: | 28.1103 | 12.2074 |
| 25 mv haze: | 27.9753 | 12.1169 |
| 50 mv haze: | 27.8412 | 12.0240 |
| 75 mv haze: | 27.7033 | 11.9341 |
| 100 mv haze: | 27.5718 | 11.8323 |
| spotSize = 44 um | | |
| 0 mv haze: | 29.4332 | 12.7819 |
| 25 mv haze: | 29.2914 | 12.6894 |
| 50 mv haze: | 29.1505 | 12.5937 |
| 75 mv haze: | 29.0097 | 12.4958 |
| 100 mv haze: | 28.8632 | 12.4009 |
| spotSize = 45 um | | |
| 0 mv haze: | 30.7855 | 13.3706 |
| 25 mv haze: | 30.6374 | 13.2739 |
| 50 mv haze: | 30.4897 | 13.1747 |
| 75 mv haze: | 30.3426 | 13.0736 |
| 100 mv haze: | 30.1940 | 12.9720 |
| spotSize = 46 um | | |
| 0 mv haze: | 32.1695 | 13.9703 |
| 25 mv haze: | 32.0149 | 13.8701 |
| 50 mv haze: | 31.8609 | 13.7670 |
| 75 mv haze: | 31.7068 | 13.6616 |
| 100 mv haze: | 31.5482 | 13.5619 |
| spotSize = 47 um | | |
| 0 mv haze: | 33.5832 | 14.5852 |
| 25 mv haze: | 33.4214 | 14.4826 |
| 50 mv haze: | 33.2592 | 14.3775 |
| 75 mv haze: | 33.0961 | 14.2715 |
| 100 mv haze: | 32.9347 | 14.1641 |
| spotSize = 48 um | | |
| 0 mv haze: | 35.0273 | 15.2121 |
| 25 mv haze: | 34.8582 | 15.1059 |
| 50 mv haze: | 34.6890 | 14.9972 |
| 75 mv haze: | 34.5210 | 14.8870 |
| 100 mv haze: | 34.3531 | 14.7734 |
| spotSize = 49 um | | |
| 0 mv haze: | 36.5022 | 15.8521 |
| 25 mv haze: | 36.3260 | 15.7426 |
| 50 mv haze: | 36.1504 | 15.6298 |
| 75 mv haze: | 35.9753 | 15.5161 |
| 100 mv haze: | 35.7947 | 15.4050 |
| spotSize = 50 um | | |
| 0 mv haze: | 38.0074 | 16.5064 |
| 25 mv haze: | 37.8238 | 16.3937 |
| 50 mv haze: | 37.6411 | 16.2775 |
| 75 mv haze: | 37.4577 | 16.1603 |
| 100 mv haze: | 37.2752 | 16.0397 |

TABLE 1-continued

Volume = A * log10 (Extension Factor) + B

| | A | B |
|---|---|---|
| spotSize = 51 um | | |
| 0 mv haze: | 39.5428 | 17.1725 |
| 25 mv haze: | 39.3514 | 17.0559 |
| 50 mv haze: | 39.1618 | 16.9355 |
| 75 mv haze: | 38.9702 | 16.8158 |
| 100 mv haze: | 38.7807 | 16.6925 |
| spotSize = 52 um | | |
| 0 mv haze: | 41.1084 | 17.8535 |
| 25 mv haze: | 40.9102 | 17.7325 |
| 50 mv haze: | 40.7102 | 17.6115 |
| 75 mv haze: | 40.5134 | 17.4857 |
| 100 mv haze: | 40.3118 | 17.3659 |
| spotSize = 53 um | | |
| 0 mv haze: | 42.7053 | 18.5456 |
| 25 mv haze: | 42.4985 | 18.4223 |
| 50 mv haze: | 42.2927 | 18.2957 |
| 75 mv haze: | 42.0865 | 18.1676 |
| 100 mv haze: | 41.8781 | 18.0413 |
| spotSize = 54 um | | |
| 0 mv haze: | 44.3316 | 19.2529 |
| 25 mv haze: | 44.1161 | 19.1266 |
| 50 mv haze: | 43.9032 | 18.9950 |
| 75 mv haze: | 43.6899 | 18.8631 |
| 100 mv haze: | 43.4741 | 18.7312 |
| spotSize = 55 um | | |
| 0 mv haze: | 45.9888 | 19.9726 |
| 25 mv haze: | 45.7658 | 19.8417 |
| 50 mv haze: | 45.5424 | 19.7081 |
| 75 mv haze: | 45.3210 | 19.5724 |
| 100 mv haze: | 45.0972 | 19.4377 |

Figure 11:
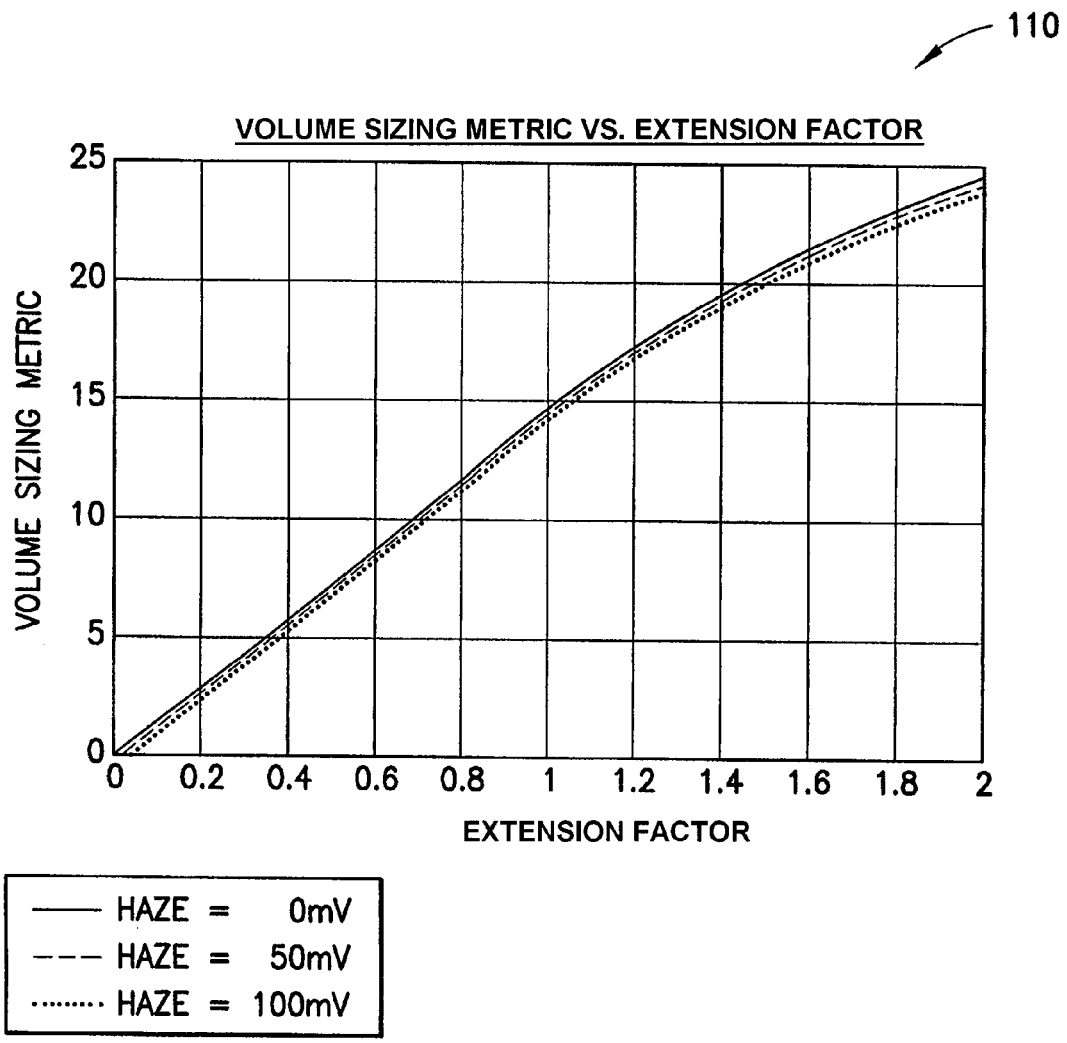
FIG. 11 is a graph illustrating a relationship between volume sizing metric and extension factor for various background haze values.

The volume sizing metric can be extended to extension factors in the range of 0-1 indicated in equations (18a) and (18b) above. In the range of 0-1, there is no non-linearity due to saturation. Accordingly, the relationship in the range on an extension factor between 0 and 1 is linear instead of semi-log. Referring to FIG. 11, the linearity of the relationship is illustrated between extension factor values of 0 and 1, while the semi-logarithmic relationship is illustrated in extension factors between 1 and 2. The overlap of the two ranges in graph 110 shows how the disclosed system and method can provide continuity of measurement across saturation or clipping thresholds. Accordingly, the same technique may be used to measure sample particles affected by saturation and sample particles that are not affected by saturation. The continuity provides an advantage for avoiding changing measurement techniques or methods over the course of a scan. Another advantage permitted by the measurement continuity is the simplification of calibration for the equipment.

The calculation of the volume sizing metric is used to ultimately size the sample defect or particle. The known relationship between volume and defect or particle size is applied to compare the calculated volume value to volume values obtained from known particle sizes. The relationship may be determined using at least one response curve showing intensity response shape volume values as a function of the extension factor for the particle size. One response curve may be represented in semi-log form to show the linear relationship between intensity response shape volume values and the log of the extension factor. This response curve may be used for extension factors greater than or equal to 1 in accordance with equations (18a) and (18b).

Alternately, the relationship may be determined using a table that contains representative intensity response shape volume values and extension factors for known particle sizes. The use of a table containing representative values may be helpful in situations in which it is desirable to obtain measurements that are less computationally intensive.

The volume sizing metric provides a simplified and straightforward means for locating and sizing defects on a wafer surface, even when the measuring equipment becomes saturated. The metric permits simple calibration of the equipment while allowing the equipment to operate in both saturated and unsaturated ranges of operation without recalibration. The disclosed system and method obtain very good correlation with actual defect sizes and consistency among defect measurements.

It will be appreciated by those of ordinary skill in the art that further modifications to and variations of the above-described extended defect sizing technique may be made without departing from the inventive concepts disclosed herein. Accordingly, the invention should not be viewed as limited except as by the scope and spirit of the appended claims.

What is claimed is:

1. A method for determining a size of a defect on a semiconductor wafer, comprising:
    obtaining a contiguous group of light intensity responses resulting from application of a light source to a surface of the wafer, the group having at least one saturated light intensity response;
    performing a calculation on each of the light intensity responses in the contiguous group to produce compensated responses to compensate for the at least one saturated light intensity response;
    combining the compensated responses to obtain a representative value of the combined compensated responses; and
    comparing the representative value to known values related to known defect sizes to obtain a measured defect size.

2. The method according to claim 1, further comprising summing the compensated responses to obtain the representative value.

3. The method according to claim 1, further comprising selecting light intensity responses with an intensity value above a given threshold.

4. The method according to claim 1, wherein performing a calculation further comprises filtering the light intensity responses.

5. The method according to claim 1, further comprising determining a value of a surface area of a discrete surface location based on in-scan spacing and cross-scan pitch.

6. The method according to claim 1, further comprising performing a calculation as follows:

$$V(x) = B*EF(x) \text{ for } EF(x) < 1$$

$$= A*\log_{10}[EF(x)] + B \text{ for } EF(x) \geq 1$$

where A and B are constants defined by characteristics of the sizing equipment, $V(x)$ is the representative value and $EF(x)$ is a function that indicates when the light intensity response includes saturated components.

7. The method according to claim 1, further comprising using one or more response curves for comparing the representative value to the known values.

8. The method according to claim 1, further comprising using one or more tables for comparing the representative value to the known values.

9. A system for determining a size of a defect on a semiconductor wafer, comprising:
   a light intensity response signal accumulator for receiving a group of light intensity response values related to discrete wafer locations, the group having at least one saturated light intensity response; and
   a processing engine for:
      manipulating the light intensity response values to obtain compensated response values to compensate for the at least one saturated light intensity response;
      combining the compensated responses to obtain a defect sizing metric value of the combined compensated responses; and
      comparing the obtained metric value with known metric values to determine a defect size.

10. A method of inspecting a semiconductor wafer for determining size and location of wafer defects by developing an equivalent voltage or power value for a defect related to defect size, comprising:
   using a first defect size estimation technique to size defects over a first defect size range, and
   using a second defect size estimation technique to size defects over a second defect size range greater than the first defect size range, wherein using said second defect size estimation technique further comprises using information obtained from said first defect size estimation technique for predicting said defect sizes,
   wherein one of the first or second defect size estimation techniques comprises,
      obtaining a contiguous group of light intensity responses resulting from application of a light source to a surface of the wafer, the group having at least one saturated light intensity response;
      performing a calculation on each of the light intensity responses in the contiguous group to produce compensated responses to compensate for the at least one saturated light intensity response;
      combining the compensated responses to obtain a representative value of the combined compensated responses; and
      comparing the representative value to known values related to known defect sizes to obtain a measured defect size.

11. The method of claim 10 further comprising:
   directing an incident beam onto a surface of the semiconductor wafer;
   wherein using said first defect size estimation technique further comprises obtaining a plurality of cross-sections of a Gaussian shape representative of said defect, and employing curve fitting and knowledge of the shape of the incident beam on the defect to determine the voltage equivalent magnitude of said defect; and
   wherein using the second defect size estimation technique further comprises determining the voltage equivalent magnitude of a defect by combining a slope value representative of a relationship between the area of a cross-section in a Gaussian pulse and a height of the pulse at the cross-section, a predetermined voltage threshold, and an estimate of a defect area at the predetermined voltage threshold.

12. The method of claim 10, wherein said information further comprises a slope value representative of a relationship between the area of a cross-section in a Gaussian pulse and a height of the pulse at the cross-section.

* * * * *